(12) United States Patent
Kerr et al.

(10) Patent No.: US 7,134,754 B2
(45) Date of Patent: Nov. 14, 2006

(54) RETINAL FUNCTION CAMERA

(76) Inventors: Patrick Kerr, 9 The Chase, Reigate, Surrey (GB) RH2 7JD; Jonathan Watts, The Old Workshops, Farringdon, Exeter, Devon (GB) EX6 2JD ( * ) Notice: Subject to any disclaimer, the term of this patent is extended or adjusted under 35 U.S.C. 154(b) by 257 days.

(21) Appl. No.: 10/474,524

(22) PCT Filed: Apr. 3, 2002

(86) PCT No.: PCT/GB02/01538

§ 371 (c)(1),
(2), (4) Date: Mar. 26, 2004

(87) PCT Pub. No.: WO02/080759

PCT Pub. Date: Oct. 17, 2002

(65) Prior Publication Data

US 2004/0156016 A1    Aug. 12, 2004

(30) Foreign Application Priority Data

| Apr. 9, 2001 | (GB) | ................................ 0108885.5 |
| May 16, 2001 | (GB) | ................................ 0111975.9 |
| Aug. 6, 2001 | (GB) | ................................ 0119155.0 |

(51) Int. Cl.
*A61B 3/14* (2006.01)

(52) U.S. Cl. .................................. 351/206

(58) Field of Classification Search ............... 351/206, 351/207, 221; 600/310, 340
See application file for complete search history.

(56) References Cited

U.S. PATENT DOCUMENTS

| 5,413,098 A | * | 5/1995 | Benaron ...................... 600/310 |
| 5,776,060 A | * | 7/1998 | Smith et al. ................... 600/340 |
| 6,149,589 A | | 11/2000 | Diaconu et al. |
| 6,198,532 B1 | | 3/2001 | Buckwald et al. |
| 6,244,712 B1 | | 6/2001 | Smith et al. |
| 6,276,798 B1 | * | 8/2001 | Gil et al. ..................... 351/206 |

FOREIGN PATENT DOCUMENTS

WO    WO 00/06017    2/2000

OTHER PUBLICATIONS

"Handheld Four-Wavelength Retinal Vessel Oximeter", Heaton et al., Ophthalmic Technologies X, Proc. SPIE, vol. 3908 (2000).

(Continued)

*Primary Examiner*—George Manuel
(74) *Attorney, Agent, or Firm*—Timothy J. Keefer; Seyfarth Shaw LLP

(57) ABSTRACT

A retinal camera is used to examine an eye, the camera including a light source having first and second sources emitting first and second wavelength bands. The first and second light sources are arranged to alternately produce light onto the retina such that the absorptivity of light of the first wavelength band by oxygenated blood is greater than the absorptivity of light of the second wavelength band, and the absorptivity of light of the first wavelength band by the oxygenated blood is less than absorptivity of light of the second wavelength band. Light is selectively focused from the first and second sources by an optical arrangement and imaging devices produce respective images of a portion of the retina illuminated with the respective wavelength bands. The images obtained by the imaging device are processed by the imaging device and processor to determine a retinal metabolic image based on haemoglobin oxygenation. In an embodiment of the invention light is scanned across the retina.

43 Claims, 3 Drawing Sheets

OTHER PUBLICATIONS

"Oximetry of Retinal Vessels by Dual-Wavelength Imaging: Calibration and the Influence of Pigmentation", Beach, J et al. App. Physiol., 86(2)748-758, 1999.

P.F. Sharp, A. Manivannan, P. Vieira, J.H. Hipwell, Laser Imaging of the Retina, Br I Ophthalmol 1999, 83: 1241-1245.

Robert Dinn, Alon Harris, Larry Kagermann, Ehud Rechtman, Rishi Kumar, Retinal and Optic Nerve Head oximetry, pp. 283-293.

* cited by examiner

RETINAL FUNCTION CAMERA

CROSS REFERENCE TO RELATED APPLICATION

This application is a U.S. National Phase of International Patent Application serial No. PCT/GB02/01538, filed Apr. 3, 2002 which claims priority of Great Britain Patent Application serial No's. 0108885.5, filed Apr. 9, 2001, 0111975.9, filed May 16, 2001 and 0119155.0, filed Aug. 6, 2001.

This invention relates to a retinal function camera.

Age-related macular degeneration may cause loss of macula function of an eye due to death of photoreceptor calls and retinal pigment epithelium. This results in the gradual loss of detailed central vision. In addition, small yellow deposits in the centre of the retina, known as drusen, are seen in the early stages of macular degeneration. People aged over 50 who have drusen are at risk of developing choroidal neovascularisation. This refers to small new abnormal blood vessels that appear to form in response to tissue hypoxia. In such neovascular age-related macular degeneration, the abnormal new blood vessels from the choroidal layer grow and proliferate with fibrous tissue within the drusen material. This choroidal neovascularisation may cause acute loss of vision as transudate or haemorrhage accumulates within or beneath the retina. The transudate, haemorrhage or scar tissue may be seen on ophthalmoscopy but fluorescein angiography may be needed to visualise the abnormal blood vessels. The area of choroidal neovascularisation may be treated by either laser photocoagulation or, if the new vessels extend under the centre of the retina, by photodynamic therapy.

However, the new blood vessels are difficult to see. Screening for the choroidal new vessels and their complications, which may develop over a short time, is currently done by identifying loss of vision. The diagnosis and assessment requires investigation by an ophthalmologist, who may need to use fluorescein angiography to see the new choroidal vessels. Current screening for choroidal neovascularisation involves a patient observing straight lines on a piece of graph paper and reporting any distortion of the lines or the development of blank spots.

Alternatively, any change of retinal metabolism, such as macular degeneration and diabetic retinopathy, may be assessed by studies of the oxygenation of blood in the retina. Arterial blood is highly oxygenated while venous blood is deoxygenated. Areas of retinal tissue hypoxia may be recognised before the development of new vessels.

The oxygenation of blood in the retina can be determined by illuminating the blood with infrared light of different wavelengths due to differential absorption of different wavelengths by oxygenated and deoxygenated blood. Deoxygenated blood illuminated at 760 nm appears darker than when it is illuminated at 1000 nm. Conversely oxygenated blood illuminated at 760 nm appears lighter than when illuminated at 1000 nm. In illumination at both 760 nm and 1000 nm partially deoxygenated blood appears on a grey scale.

It is known from U.S. Pat. No. 4,877,322 to use this property to measure relative oxygen saturation of choroidal blood of the eye fundus and more particularly to make such measurements in specifically selected areas of the eyegrounds for the study of glaucoma and macular degeneration. In this prior art disclosure the retina is illuminated simultaneously with white, red and infrared light and the relative absorption of red and infrared light used to determine the oxygenation and, hence, the concentration of capillaries in regions of the retina. However, because the retina is illuminated with all three wavelengths simultaneously, it is not possible to obtain any detailed view of retinal function.

It is known from U.S. Pat. No. 5,219,400 to determine the degree of haemoglobin oxygenation in the blood vessels of the retina under conditions of dark-adaptation and light-adaptation by directing a beam of near-infrared light having a range of wavelengths from 700–100 nm at a blood vessel in the retina, measuring the intensity of the backscattered light from the blood vessel in the range from 700 to 800 nm at regularly spaced intervals of wavelength such as 2 nm, and determining the degree of haemoglobin oxygenation by reference to a correlation between haemoglobin oxygen and light absorbance in the near-infrared spectral range. There is also disclosed an artificial eye model for calibration of haemoglobin oxygen saturation and near infrared reflective spectral data. However, there is no disclosure of the formation of an image of retinal function.

U.S. Pat. No. 5,400,791 discloses the use of infrared laser light between 795 nm and 815 nm for angiography.

U.S. Pat. No. 6,244,712 discloses the use of sequential scan lines illuminated with alternate lasers to form an interlaced data frame, and the use of an r-wave of an electrocardiogram to trigger laser illumination of a retina.

It is an object of the present to at least mitigate the foregoing difficulties.

According to a first aspect of the invention there is provided a retinal function camera comprising: a first source of light of a first wavelength band; a second source of light of a second wavelength band, the absorptivity of light of the first wavelength band by oxygenated blood being greater than the absorptivity of light of the second wavelength band and the absorptivity of light of the first wavelength band by deoxygenated blood being less than absorptivity of light of the second wavelength band; means for focusing light selectively from the first and second sources on a portion of a retina of an eye; imaging means for producing respective images of a portion of the retina illuminated with the respective wavelength bands; and processing means adapted to process the respective images obtained by the imaging means to determine isoreflective points of the respective images at which absorption of light of the first wavelength is substantially equal to absorption of light of the second wavelength and areas of the respective images having differential absorptivity for the first and second wavelengths, to obtain a retinal function image based on haemoglobin oxygenation.

Conveniently, the processing means comprises means for displaying the respective images alternately, at a predetermined frequency, such that the areas of the respective images having differential absorptivity at the first and second wavelengths, flicker.

Preferably, the predetermined frequency is 12 Hz.

Advantageously, the first and second wavelength bands are selected between 488 nm and 1000 nm, to produce a functional image.

Conveniently, the first wavelength band is centred substantially on 830 nm and the second wavelength band is centred substantially on one of 635 nm and 670 nm and 760 nm; or the first wavelength band is centred substantially on 910 nm and the second wavelength band is centred substantially on one of 635 nm and 670 nm and 760 nm.

Conveniently, there is provided an array of superluminescent diodes producing light in the wavelength band 550 to 650 nm to produce a conventional image and the second wavelength band is 700 nm to 805 nm and the first wavelength band is 805 nm to 1000 nm to produce a functional image.

Advantageously, the processing means comprises means for assigning the respective images created with the first wavelength band and the second wavelength band and the conventional image with false colours respectively and combining the three images to form a combined colour image.

Conveniently, the first source of light is a laser.

Advantageously, the second source of light is a laser.

Conveniently, the first and second sources of light are superluminescent diodes provided with narrow band pass filters to restrict the waveband of light emitted.

Alternatively, a wide spectrum light source is provided wavelengths from near infrared through the visible spectrum and the first and second light sources are produced by passing the wide spectrum light through narrow band pass filters.

Conveniently, the means for focusing light selectively from the first source and the second source comprise means for focusing light from the first and second sources and for sequentially switching on and off the first and second sources alternately.

Alternatively, the means for focusing light selectively from the first and second sources comprise means for focusing light from the first and second sources and shutter means for alternately interrupting light from the first and second sources, respectively.

Conveniently, the processing means includes means for comparing an image with a reference image formed at an earlier time.

Preferably, the processing means includes pattern recognition means for aligning the image with the reference image.

Advantageously, the processing means includes means for assigning first areas of the respective images having differential absorptivity for the first and second wavelets corresponding to portions of the retina having greater oxygenation than the isoreflective points a first false colour and for assigning second areas of the respective images having differential absorptivity for the first and second wavelengths corresponding to portions of the retina having less oxygenation than the isoreflective points a second false colour and for generating intensities of the false colours at each point in the image proportional to the difference in oxygenation of that respective point from the oxygenation of the isoreflective points.

Preferably, a wavelength or power of the first source and/or the second sour is variable to tune the isoreflective point.

Conveniently the processing means includes means for calibrating oxygenation by identifying a portion of the retina image of maximum oxygenation and a portion of the retina image of maximum de-oxygenation.

Advantageously, the means for focusing light include scanning means for scanning the focused light across at least a portion of the retina.

Conveniently, the scanning means include first scanning means for scanning the focused light horizontally across the at least a portion of the retina and second scanning means for scanning the focused light vertically across the at least a portion of the retina.

Preferably, the first scanning means includes one of a rotatable polygonal mirror and a vibratable plane mirror.

Advantageously, the second scan means includes a galvanometer scanner.

Conveniently, first synchronising means are provided to synchronise the first and second scanning means with selection means for selectively operating the first source of light and the second source of light.

Advantageously, second synchronising means are provided to synchronise the first and second scanning means with the imaging and processing means.

Conveniently, the first and second scanning means are adapted to de-scan light reflected from the retina and reflecting de-scanned light to the imaging and processing means.

Advantageously, the first and second scanning means operate at frequencies corresponding to television scanning frequencies such that the imaging and processing means may be used to form a television image.

Conveniently, at least one of a confocal filter is provided locatable upstream of the imaging and processing means for detecting a retinal surface image and for blocking a deeper choroidal image and an anti-confocal filter locatable upstream of the imaging and processing means to block the retinal surface image and allow the deeper choroidal image to be detected.

Advantageously, a first linear polarising filter is provided between the light source and the eye and a second poling filter orthogonal to the first linear polarising filter is provided between the eye and the imaging and processing means such that the second orthogonal polarising filter blocks light reflected from a surface of the eye.

Conveniently, an optical beam adder is provided for allowing a first laser beam from the first light source and a second laser beam from the second light source access to an optical axis of the retinal function cameras.

Preferably, the processing means includes an imaging device sensitive to light emitted by the first source of light and the second source of light.

Conveniently, the imaging device is one of a CMOS array, a CCD array, a photodetector or an infrared image sensor.

Advantageously, optical fibre and lens means re provided for producing a point source of light from light from the first source of light and light from the second source of light.

According to a second aspect of the invention, there is provided a method of obtaining a retinal function image based on haemoglobin oxygenation, the method comprising the steps of providing a retinal function camera having a first source of light of a first wavelength band and a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of tic second wavelength band; focusing light selectively from the first and second sources on a portion of a retina of an eye; producing respective images of the portion of the retina illuminated with the respective wavelength bands; and processing the respective images to determine isoreflective points of the respective images at which absorption of light of the first wavelength is substantially equal to absorption of light of the second wavelength and areas of the respective images having differ absorptivity for the first and second wavelengths to obtain a retinal function image based on haemoglobin oxygenation.

Conveniently, the step of processing the images comprises: assigning to first portions of the image corresponding to portions of the retina having greater oxygenation than the isoreflective point a first false colour and generating intensity of the false colours at each point in the image proportional to the flicker contrast that is proportional to the difference in oxygenation of that respective point from the oxygenation of the isoreflective point, assigning to second portions of die image corresponding to portions of the retina having less oxygenation than the isoreflective point a second false colour and generating intensity of the false colours at each point in the image proportional to the flicker contrast that is proportional to the difference in oxygenation of that respective point from the oxygenation of the isoreflective point, assigning a third colour to the isoreflective point, and constructing a composite image by combining the first, second and third colour age data to form a colour image of retinal function based on haemoglobin oxygenation data.

Preferably, the first colour is red.

Preferably, the second colour is blue.

Preferably, the third colour is yellow.

Specific embodiments of the invention will now be described by way of example with reference to the accompanying drawings in which.

In the diagrams, like reference numerals-denote like parts.

Figure 1:
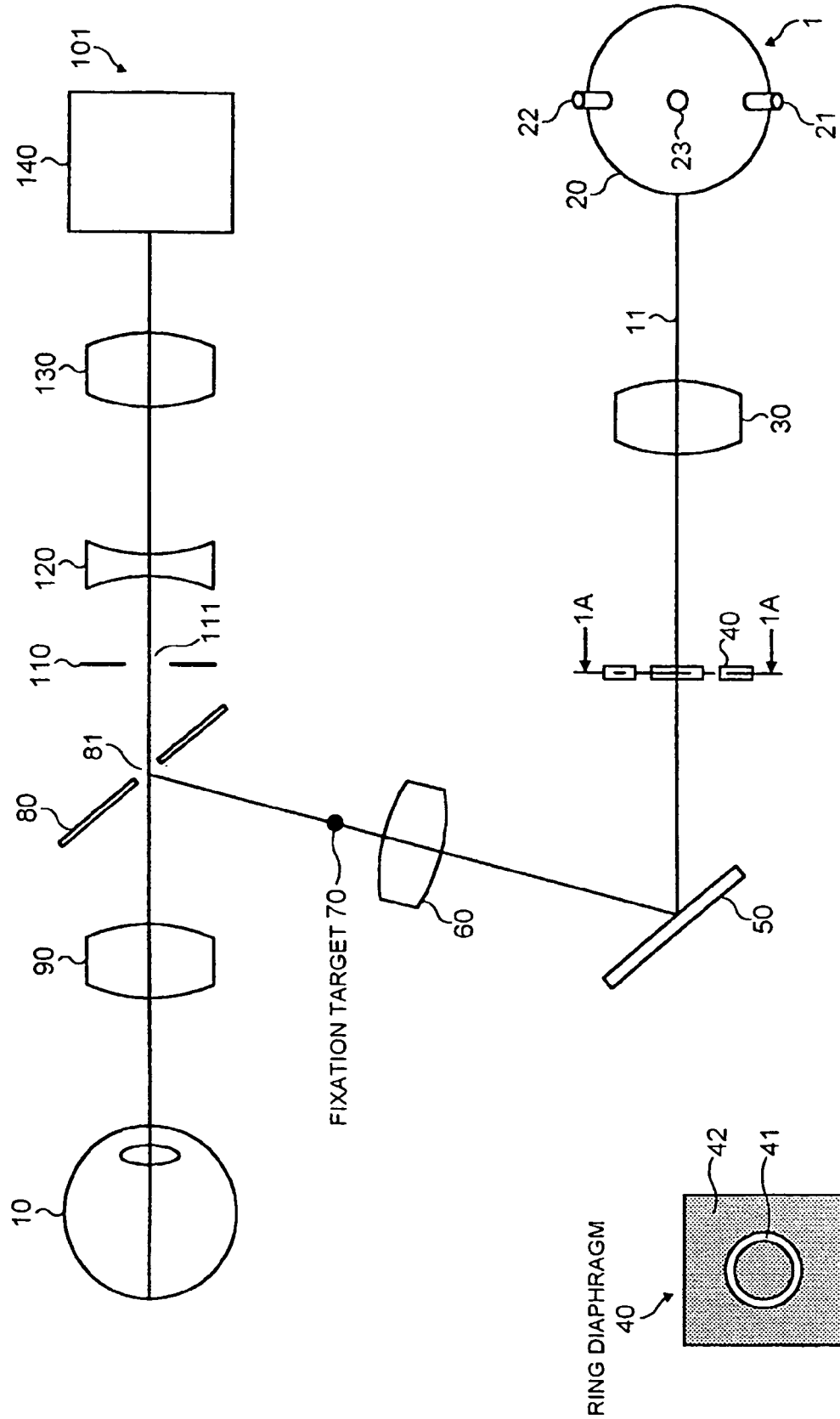
FIG. 1 shows a first embodiment of the invention in schematic form.

Referring to FIG. 1, a retinal camera 101 is used to examine an eye 10. The camera includes a light source 1 comprising an integrating sphere 20 having first and second sources 21,22 disposed at substantially 120° to each other, emitting first and second infrared wavelength bands respectively and a visible light source 23, to provide diffuse illumination. The primary function of the integrating sphere is to produce alternating infrared light from the same point source so that the retinal images, formed by the two infrared sources 21,22, are aligned. The 600 nm visible light source 23 is useful in differentiating veins and arteries in the retinal image. It is present to allow a functional image obtained with the infrared sources to be compared with a conventional image.

The functional image may be generated by contrasting images obtained from both the visible (450–700 nm) and infrared (700–1000 nm) spectra. The infrared haemoglobin oxygen saturation light absorption is well defined-between 700–805 nm and 805–1000 nm. The visible spectrum has a complex haemoglobin light absorption relationship as disclosed in Van Assendelft OW. Spectrophotometry of haemoglobin derivatives. Royal Vangorcum, Assen, The Netherlands: Thomas, 1970. Blue light between 450 nm and 500 nm may be contrasted with red light between 600 nm and 700 nm to generate a functional image. The blue light in the range 450–500 nm may also be contrasted with the near infrared 700–805 nm light.

Thus, light between 450 nm and 1000 nm may be used. Suitable pairs of wavelengths are: 488 nm and 600 nm or 635 nm or 670 nm or 760 nm; or 635 nm and 830 nm or 910 nm; or 670 nm and 830 nm or 910 nm; or 760 nm and 830 nm or 910 nm.

Possible sources of illumination include an array of superluminescent diodes, producing light in the range 550 nm to 650 nm, and preferably at 600 nm, to produce a conventional image and superluminescent diodes sequentially illuminating a diffuse reflective integrator sphere with infrared light in the region of 758 nm (700 nm–805 nm) and 910 nm (805 nm–1000 nm) to provide illumination for a functional image. Narrow bandpass filters may be used with the superluminescent diodes to restrict their bandwidth. Alternative optical arrangements for the light source include a beam splitter arrangement for the near infrared superluminescent diodes. The superluminescent diodes may either switch on and off sequentially or their light be sequentially blocked with a shutter. Alternative light sources may be used. For example a wide spectrum source emitting radiation from near infrared through the visible spectrum such as a xenon light doped with other gases to provide a near infrared spectrum between 700 nm to 1000 nm with narrow band pass filters may be used. Alternatively, laser diodes may be used as the infrared sources, in which case to avoid the speckle effect of laser light, the integrating sphere 20 converts collimated, coherent, narrow band light from the laser diodes into uncollimated, incoherent, narrow band light. It will be understood that alternative apparatus for producing a point source of light formed from the first source of light and second source of light may be used, for example, an optical fibre and lens apparatus may replace the integrating sphere, and dichroic beam combiner or half silvered mirror.

Figure 1A:
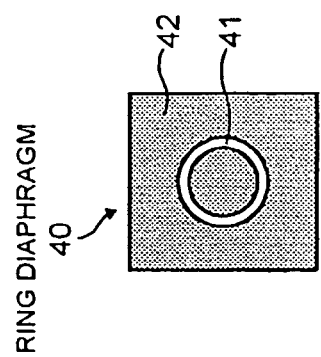
FIG. 1A shows a cross-section along the double arrow headed line 1A—1A of FIG. 1.

Light from the light source is collimated by a condenser lens 30 and passed through an annular ring diaphragm 40 before being reflected by a mirror 50 and passing through a relay lens 60. A cross-section of the annular ring diaphragm is shown in FIG. 1A, in which is shown an annular transparent portion 41 within an opaque support 42. A cone of light emergent from the annular diaphragm and reflected by the mirror 50 is then reflected by a perforated mirror 80, having a central transmission hole 81, through an objective lens 90 into the eye 10 to produce an evenly illuminated area at a focal plane of the eye 10. An internal fixation target 70 is provided between the relay lens 60 and the perforated mirror 80, on an optical axis defined thereby. The internal fixation target 70 may be a small illuminated object such as cross-wires on which the eye 10 may be focussed. After absorption within the retina, light is reflected from the retina out of the eye back through the objective lens 90 and a portion of the reflected light passes through the central aperture 81 of the perforated mirror 80, and sequentially through an occluding diaphragm 110, a focus lens 120 and an imaging lens 130 to form an image in an image recorder and processor 140. The annular rig diaphragm 40 and the pupil of the eye 10 are arranged in conjugate positions in the illuminating optical system and the pupil of the eye 10, transmission hole 81 of the mirror 80 and the aperture 111 of the occluding diaphragm 110 are arranged in conjugate positions of the objective optical system.

Figures 2, 2A:
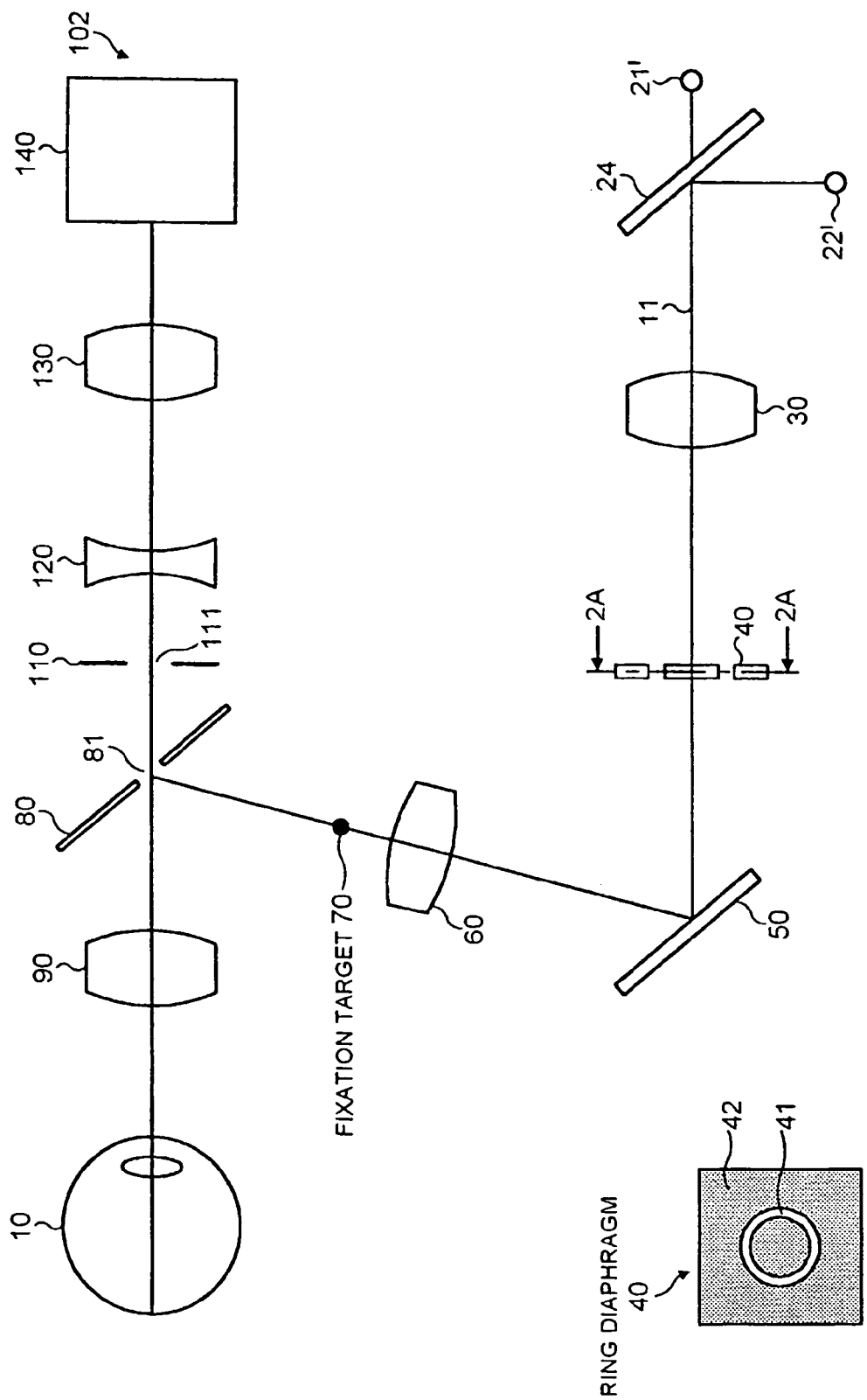
FIG. 2 shows a second embodiment of the invention in schematic form.
FIG. 2A shows a cross-section along the double arrowhead lines 2A—2A of FIG. 2.

FIG. 2 illustrates a further embodiment 102 of the invention in which the integrating sphere of the first embodiment shown in FIG. 1 is replaced by a half silvered mirror 24 and two superluminescent diodes with narrow band pass filters 21',22' are disposed so that infrared light of a first waveband from the first superluminescent diode 21' passes through the mirror along the optical axis 11 and infrared light of a second waveband from the superluminescent diode 22' is reflected by the half silvered mirror 24 to also pass along the optical axis 11. Other parts of the embodiment are as described for the first embodiment illustrated in FIG. 1.

The operation of the two embodiments of the invention is similar. Taking the second embodiment of FIG. 2 as an example, with the patient focusing the eye 10 to be studied on the fixation target 70 the pupil of the eye is located adjacent to the aspheric ophthalmic objective lens 90. This aligns the pupil and the foveola to ensure that when the light source is activated to illuminate the retina, light is transmitted through the pupil rather than reflected from the iris. Without an illuminated object the eye would wander while looking into a black void. The illuminated object is faint in intensity to avoid pupil constriction. A typical illuminated object is a fine cross or concentric circle cut out of an opaque screen in front of a low-powered light-emitting diode. An alternative would be illuminated cross-wires.

Either visible 600 nm light from a superluminescent diode or xenon light source (not shown) is used to obtain a conventional image. Alternating infrared illumination in the region of 758 nm and 910 nm is provided by the superluminescent diodes 21',22' to project infrared light beams onto the retina to obtain a functional image.

The image recorder and processor 140 comprises an imaging device sensitive to light in the designated spectrum, for example a CMOS or CCD array, photodetector, infrared or visible light sensor, or other infrared image sensor.

In order to analyse the images, account must be taken of residual internal reflection inside the optical system. This is minimised by a black absorptive internal surface and the use of ridging or internal baffles. In addition, the light output from the light source may be variable and light is absorbed by the front surface coatings of the mirrors and the lenses. Further, light may leak into the system from around an eye seal which may produce a light flare and in some patients, vasoconstriction due to drugs and smoking may alter the retinal oxygenation. These problems may be largely obviated by comparing the images produced under different wavelength illuminations or at different times.

A visualisation of altered retinal function or structure may be obtained by comparing individual retinal field images with initial reference retinal field images to detect any change. This involves the use of pattern recognition software to obtain a "best fit" superimposition of the reference and new image. The reference image is then subtracted from the new image leaving the components that have changed. The components that have changed are then superimposed on the new image and identified by, for example, a colour change or flashing image. Alternatively, the three images obtained with the visible light and two infrared wavelengths from the superluminescent diode sequential illumination may be superimposed, after allocating each image a false colour (for example, red, green and blue), to create a colour image.

As indicated above, deoxygenated blood illuminated at 760 nm appears darker than when it is illuminated at 1000 nm. Conversely oxygenated blood illuminated at 760 nm appears lighter than when illuminated at 1000 nm. In both images partially deoxygenated blood would appear on the grey scale.

Therefore, if alternating images are displayed, at for example 12 Hz, on a screen most of the images of blood vessels will flicker but there will be areas of blood vessels that do not flicker in light intensity. These non-flickering blood vessels at the isoreflective point for equal energy illumination form a reference deoxygenation point. The non-flickering, isoreflective areas may be displayed in yellow. Areas that flicker have a significant difference in oxygenation from the isoreflective point. The greater the contrast of flicker the more saturated or desaturated the blood is with oxygen. The desaturated blood may be displayed in blue and the colour intensity related to the flicker contrast. The oxygenated blood may be displayed in red and the colour intensity related to the flicker contrast. This produces a subjective image of retinal function with one isoreflective point.

The isoreflective point, of a composite image formed by the first and second light sources, may be tuned by varying the wavelength or power of either or both of the light sources.

To determine absolute values of oxygenation it is necessary to calibrate the image. A retinal artery with maximum flicker contrast when illuminated with 900 nm–1000 nm near infrared light is examined. An inspired oxygen concentration $FiO_2$ is increased from 21% to, for example, 50% to ensure that the retinal artery blood is 100% saturated. This provides a reference for 100% oxygen saturation of retinal blood. A retinal haemorrhage with maximum flicker contrast when illuminated with near infrared light in the region of 760 nm is examined. The retinal haemorrhage consists of deoxygenated blood. The inspired oxygen concentration $FiO_2$ may be decreased from 21% to 10% to ensure that there is no increase in flicker contrast or the $FiO_2$ may be increased to 50% to ensure that there is no reduction in flicker contrast. This provides a reference for deoxygenated retinal blood. Alternative calibration may be obtained by perfusing either an animal eye or artificial eye model with haemoglobin of known oxygen saturation and recording infrared images. This technique may be used to obtain a haemoglobin oxygen saturation level for the isoreflective point. The retinal function calibration techniques outlined may be repeated for cytochrome $a,a_3$, with infrared light in the range 700 nm to 1300 nm, to obtain a further isoreflective point and additional calibration. Cytochrome $a,a_3$ is used in addition to haemoglobin oxygen saturation to assess tissue oxygenation states. However, the longer wavelengths used would have greater tissue penetration and a possible degraded image quality.

Alternatively, an artificial eye model with three channels of blood may be used for haemoglobin oxygen calibration. The eye model has a first reference channel containing 50% oxygen saturated blood, a second reference channel containing 100% oxygen saturated blood and a third assessment channel containing blood with variable haemoglobin oxygen saturation.

Figure 3:
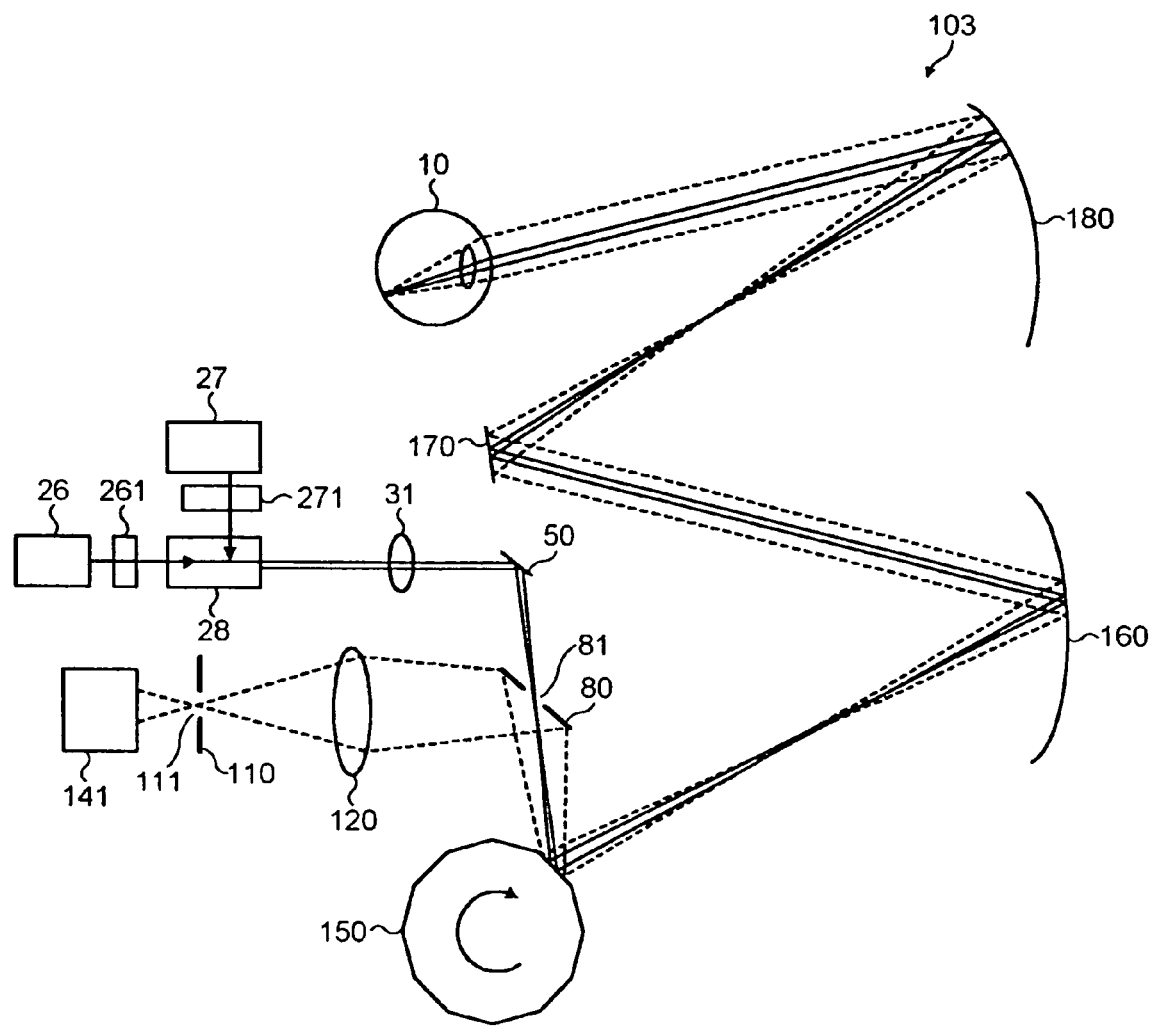
FIG. 3 shows a third embodiment of the invention in schematic form.

FIG. 3 illustrates a scanning laser retinal function camera which is a third embodiment of the invention. This produces sequential images of the fundus from two lasers 26,27.

The scanning laser retinal function camera 103, produces sequential near infrared images of the fundus required to generate the functional image. The camera comprises a multiple near infrared laser source that is able to direct a narrow beam of infrared laser light in the region of 758 nm (700 nm–805 nm) via a mirror system and focus the light onto the fundus. The light reflected from the fundus is directed to an infrared detector, which produces an electrical output proportional to the intensity of the detected infrared light. By moving the mirror system according to a scanning sequence in a raster fashion and synchronising the detector to the scanning sequence, it is possible to produce an image of the fundus. The electrical output from the infrared detector is processed to display an image of a portion of the fundus. The laser light in the region of 758 nm (700 nm–805 nm) is then switched off and a narrow beam of infrared light in the region of 910 nm (805 nm–1000 nm) is focussed via the mirror system onto the fundus. The infrared light in the region of 910 nm which is reflected from the fundus is directed to the infrared detector which produces an electrical output proportional to the intensity of the detected light. The electrical output is processed to display an image of a portion of the fundus.

The two images obtained are stored and then processed to be displayed alternately, at a predetermined frequency, to form a composite image such that areas that have a differential absorptivity at the 700 nm–805 nm and 805 nm–1000 nm wavelengths flicker. Non-flickering, isoreflective blood vessels contain partially oxygenated haemoglobin at which the absorption of light from the 700 nm–805 nm laser is equal to the absorption of light from the 805 nm to 1000 nm laser. The non-flickering isoreflective areas may be displayed in yellow. Blood vessels that flicker have a significant difference in oxygenation from the isoreflective point. The greater the contrast of the flicker the more saturated or desaturated the blood is with oxygen. The desaturated blood may be displayed in blue and the colour intensity related to the flicker contrast. The oxygenated blood may be displayed in red and the colour intensity related to the flicker contrast. This produces a subjective scanning laser image of retinal function with one isoreflective point.

The third embodiment will now be described in detail.

The scanning laser retinal function camera 103 has two separate laser beam sources, a first laser source 26 producing infrared laser light in the region of 758 nm (700 nm–805 nm), and a second laser source 27 producing infrared laser light in the region of 910 nm (805 nm–1000 nm). Infrared laser beams from the first and second sources pass through respective electrooptic modulators 261, 271, which provide individual intensity control of the respective infrared beams. An optical beam adder 28 located to receive laser beams emergent from the respective electrooptic modulators allows both infrared laser beams access to an optical axis of the scanning laser retinal function camera. This allows the infrared laser sources sequentially to illuminate a retina at the focal plane of an eye 10. The laser beam from the adder 28 passes through a focus lens 31, which allows the laser beam to be focused on the retina. The light from the focus lens 31 is reflected by a mirror 50 and passes through a central transmission hole 81 in a perforated mirror 80 onto a rotating eighteen-facet polygonal mirror 150 rotatable at about 52,100 rpm. (For clarity, a 12-facet polygonal mirror 150 is illustrated). A half-silvered mirror may be used in place of the perforated mirror 80, and such a half-silvered mirror may be constructed to have a greater reflectance of light than transmission of light. The rotatable polygonal mirror 150 reflects the infrared laser light beam onto a concave mirror 160 as a linear horizontal scan with a repetition rate of 15,625 Hz corresponding to a closed circuit television standard, in a horizontal axis of the eye 10. The concave mirror 160 reflects and focuses the infrared laser light beam onto a movable galvanometer mirror 170. The galvanometer mirror 170 is electrically movable so as to vary the reflection angle to produce a vertical scan with a repetition rate of 50 Hz in a vertical axis of the eye 10. The infrared laser light is reflected by the galvanometer mirror 170 to a concave mirror 180, which focuses the infrared laser light as a 10 micron diameter spot onto the focal plane of the eye 10.

It will be understood that alternative apparatus for producing a scanning beam may be used, for example, a vibrating mirror and galvanometer two-axis scanner may replace the polygonal mirror and galvanometer scanner.

Light reflected from the retina returns along the same pathway and is de-scanned by the galvanometer mirror 170 and the rotating polygonal mirror 150. The reflected light is then reflected by perforated mirror 80, or a half-silvered mirror, towards a focussing lens 120 and sequentially through an occluding diaphragm 110 and onto an infrared detector such as an avalanche photodiode and processor 141. The return signals are detected on a pixel-by-pixel basis and then transferred to a frame grabber card (not shown) to construct a synchronised data frame. The data frame is synchronised to the vertical frame, horizontal line and pixel clock signals from the scanning apparatus. A controller (not shown), that receives horizontal and vertical synchronising signals from the scanning apparatus, activates and deactivates the lasers sequentially.

The digital image processing is performed by a computer using digital image processing software such as Matlab™ available from The MathWorks Inc, 3 Apple Hill Drive, Natick Mass. 01760-2089, United States and Labview™ available from National Instruments Corporation, Austin Tex., United States. The isoreflective point is defined. The flicker contrast of each pixel, to the isoreflective point, is determined. A false colour, red or blue, is allocated to each pixel and the intensity of colour related to flicker contrast. The isoreflective point is allocated yellow. A composite image is constructed by combining the red, yellow and blue image data.

The scanning laser retinal function camera illustrated in FIG. 3 is similar to the Digital 35 Laser Scanning Fundus Camera, described by Plesch et al. in Applied Optics, Vol. 26, No. 8, page 1480–86, Apr. 15, 1987. This device-uses a collimated laser beam focussed by the eye to a spot of 10–15 microns diameter for illumination of a single point of the retina. The light scattered back from the retina, normally 3–5% of the incident light, is collected through the outer 95% of the pupil. Angular scanning of the illuminating laser beam sweep the spot across the retina and results in time resolved sequential imaging of the retina. The device is connected to a digital image buffer and a microcomputer for image storage and processing.

The scanning laser retinal function camera illustrated in FIG. 3 contains an optical beam adder that is used in U.S. Pat. No. 6,099,127. This uses a red 670 nm, green 540 nm and blue 488 nm laser light sources, with an optical beam adder, which separately illuminate the fundus. The three images obtained are used to construct a colour representation of the fundus.

Optimising the Retinal Function Image

The ideal retinal function image contains:
  a stable non-flickering background of light reflected from retinal and choroidal pigments and cells;
  maximal contrast of light from deoxygenated and oxygenated blood; and
  similar depth of infrared light retinal penetration to image the same retinal and choroidal components.

The retinal function image may be time synchronised with an R wave of a patient's electrocardiogram, to allow retinal metabolism to be studied at different phases of the cardiac cycle. The data frame from which the retinal function image is constructed by the digital image processor consists of data from (in this example) the 512 scan lines each scanned with, at least, two wavelengths of light. The data frame "starts" at line 1 and "ends" at line 512. Alternatively, the R wave of the electrocardiogram may be used as a time signal to define the next line scan x as the start of the R wave synchronised data frame. The retinal function image is then constructed by the digital processor from a data frame defined by line x to line 512 and the next line 1 to line x−1. A time delay may be selected by the operator between the R wave electrocardiogram time signal and scan line x.

Infrared light in the region of 758 nm and 1000 nm may provide maximum contrast for haemoglobin oxygenation. In order to optimise the functional retinal image the 1000 nm wavelength illumination may need to be tuned closer to 805 nm. A retinal background isoreflective non-flickering point will be determined when the light energy reflected from retinal and choroidal pigment cells by the 700 nm–805 nm and 805 nm–1000 nm sources is equal. This will provide a stable non-flickering background on which to contrast the functional image. The light source wavelength or power may be variable to allow tuning of the image.

The individual light source intensity may be controlled by altering the supply power using a current limiting technology. Alternatively the light output may be controlled with either a variable aperture diaphragm or an electrooptic modulator.

Alternative Light Wavelengths

Alternative wavelengths of the light spectrum where there are significant differences of light absorption between oxyhaemoglobin and deoxyhaemoglobin may be used to generate the functional image. Light between 488 nm and 1000 nm may be used. Suitable wavelengths are 488 nm and 600 nm, 630 nm, 635 nm, 670 nm, or 760 nm; 635 nm and 830 nm or 910 nm; 670 nm and 830 mm or 910 nm; 760 nm and 830 nm or 910 nm. The visible light, between 488 nm and 700 nm, would have less retinal tissue penetration than the near infrared light.

Alternative Imaging Technology

Alternative imaging arrangements may be used to generate the separate wavelength retinal and choroidal images needed to generate the functional retinal image. The scanning laser retinal function camera may have a confocal filter positioned upstream of the detector to allow the retinal surface image to be detected while blocking the deeper choroidal image. A confocal filter is used to generate optical sections. An anti-confocal filter may be positioned upstream of the detector to block the retinal surface image and allow a deeper choroidal image to be detected.

A three dimensional retinal metabolic image may be formed by integrating a series of confocal optical sections obtained at sequential depths.

The scanning laser retinal function camera may have an orthogonal polarising filter positioned upstream of the detector. The function of the orthogonal polarising filter is to block the surface reflected light that has the same linear polarisation as the laser illumination light. This will allow orthogonally polarised light that has been scattered and reflected from deeper layers to be detected and form the image. The polarising filters therefore improve contrast by blocking surface reflections.

The retinal function camera may have a linear polarising filter on the illuminating axis and an orthogonal polarising filter on the imaging axis. The orthogonal polarising filter will block the reflected light from the retinal surface that has the same linear polarisation as the illumination light. This will allow light from deeper layers, that contain haemoglobin oxygenation information, to be detected and form the image.

The scanning laser retinal function camera controller sequentially activates the different wavelength lasers, which the scanner scans across a portion of the retina to form a complete data frame with each laser. Preferably, each scan line, rather than each frame, may be scanned twice, with alternate wavelengths, to minimise movement artefacts between two retinal images. The portion of the retina scanned sequentially, with alternate wavelengths, may be less than a scan line, such as a pixel, or it may be greater than a scan line, such as a flame. That is, the portion of a retina scanned with each alternate wavelength may correspond to a pixel, a line scan or a frame in the image formed from the scans. Sequentially scanning each line twice maximises the signal to noise ratio while minimising retinal light exposure.

Alternatively, a portion of the retina scan, such as sequential scan lines may be illuminated. This would form an interlaced data frame. The data frame would need to be deinterlaced to form the two separate images prior to constructing the retinal function image.

Simultaneous illumination of the retina with two separate wavelengths of light is possible by either using the integrating sphere or a dichroic beam combiner. The separate wavelength images may be obtained with a dichroic beam splitter and separate imaging optics.

It will be understood that although the invention has been described in relation to a retinal function camera, the invention has equal applicability to, for example, the use of a confocal microscope or multispectral camera for imaging.

The invention claimed is:

1. A retinal function camera comprising: a first source of light of a first wavelength band; a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band; means for focusing light selectively from the first and second sources on a portion of a retina of an eye; imaging means for producing respective images of a portion of the retina illuminated with the respective wavelength bands; and processing means adapted to process the respective images obtained by the imaging means to determine isoreflective points of the respective images at which absorption of light of the first wavelength is substantially equal to absorption of light of the second wavelength and areas of the respective images having differential absorptivity for the first and second wavelengths, to obtain a retinal function image based on haemoglobin oxygenation.

2. A retinal function camera as claimed in claim 1, wherein the processing means comprises means for displaying the respective images alternately, at a predetermined frequency, such that the areas of the respective images having differential absorptivity at the first and second wavelengths, flicker.

3. A retinal function camera as claimed in claim 2, wherein the predetermined frequency is 12 Hz.

4. A retinal function camera as claimed in claim 1, wherein the first and second wavelength bands are selected between 488 nm and 1000 nm, to produce a functional image.

5. A retinal function camera as claimed in claim 1, wherein the first wavelength band is centred substantially on 830 nm and the second wavelength band is centred substantially on one of 635 nm and 670 nm and 760 nm; or the first wavelength band is centred substantially on 910 nm and the second wavelength band is centred substantially on one of 635 nm and 670 nm and 760 nm.

6. A retinal function camera as claimed in claim 1, wherein there is provided an array of superluminescent diodes producing light in the wavelength band 550 nm to 650 nm to produce a conventional image and the second wavelength band is 700 nm to 805 nm and the first wavelength band is 805 nm to 1000 nm to produce a functional image.

7. A retinal function camera as claimed in claim 6, wherein the processing means comprises means for assigning the respective images created with the first wavelength band and the second wavelength band and the conventional image with false colours respectively and combining the three images to form a combined colour image.

8. A retinal function camera as claimed in claim 1, wherein the first source of light is a laser.

9. A retinal function camera as claimed in claim 8 further comprising an optical beam adder for allowing a first laser beam from the first light source and a second laser beam from the second light source access to an optical access of the retinal function camera.

10. A retinal function camera as claimed in claim 1, wherein the second source of light is a laser.

11. A retinal function camera as claimed in claim 1, wherein the first and second sources of light are superluminescent diodes provided with narrow band pass filters to restrict the waveband of light emitted.

12. A retinal function camera as claimed in claim 1, wherein a wide spectrum light source is provided emitting wavelengths from near infrared through the visible spectrum and the first and second light sources are produced by passing the wide spectrum light through narrow band pass filters.

13. A retinal function camera as claimed in claim 1, wherein the means for focusing light selectively from the first source and the second source comprise means for focusing light from the first and second sources and for sequentially switching on and off the first and second sources alternately.

14. A retinal function camera as claimed in claim 1, wherein the means for focusing light selectively from the first and second sources comprise means for focusing light from the first and second sources and shutter means for alternately interrupting light from the first and second sources, respectively.

15. A retinal function camera as claimed in claim 1, wherein the processing means includes means for comparing an image with a reference image formed at an earlier time.

16. A retinal function camera as claimed in claim 15, wherein the processing means includes pattern recognition means for aligning the image with the reference image.

17. A retinal function camera as claimed in claim 1, wherein the processing means includes means for assigning first areas of the respective images having differential absorptivity for the first and second wavelengths corresponding to portions of the retina having greater oxygenation than the isoreflective points a first false colour and for assigning second areas of the respective images having differential absorptivity for the first and second wavelengths corresponding to portions of the retina having less oxygenation than the isoreflective points a second false colour and for generating intensities of the false colours at each point in the image proportional to the difference in oxygenation of that respective point from the oxygenation of the isoreflective points.

18. A retinal functional camera as claimed in claim 17, wherein one of wavelength and power of at least one of the first source and the second source is variable to tune the isoreflective point.

19. A retinal function camera as claimed in claim 1, wherein the processing means includes means for calibrating oxygenation by identifying a portion of the retina image of maximum oxygenation and a portion of the retina image of maximum deoxygenation.

20. A retinal function camera as claimed in claim 1, wherein the means for focusing light include scanning means for scanning the focused light across at least a portion of the retina.

21. A retinal function camera as claimed in claim 20, wherein the scanning means include first scanning means for scanning the focused light horizontally across the at least a portion of the retina and second scanning means for scanning the focused light vertically across the at least a portion of the retina.

22. A retinal function camera as claimed in claim 21, wherein the second scanning means includes a galvanometer scanner.

23. A retinal function camera as claimed in claim 21, wherein first synchronising means are provided to synchronise the first and second scanning means with selection means for selectively operating the first source of light and the second source of light.

24. A retinal function camera as claimed in claim 21, wherein second synchronising means are provided to synchronise the first and second scanning means with the imaging and processing means.

25. A retinal function camera as claimed in claim 21, wherein the first and second scanning means are adapted to de-scan light reflected from the retina and reflecting de-scanned light to the imaging and processing means.

26. A retinal function camera as claimed in claim 21, wherein the first and second scanning means operate at frequencies corresponding to television scanning frequencies such that the imaging and processing means may be used to form a television image.

27. A retinal function camera as claimed in claim 20, wherein the first scanning means includes one of a rotatable polygonal mirror and a vibratable plane mirror.

28. A retinal function camera as claimed in claim 20, wherein the processing means includes means for assigning first areas of the respective images having differential absorptivity for the first and second wavelengths corresponding to portions of the retina having greater oxygenation than the isoreflective points a first false colour and for assigning second areas of the respective images having differential absorptivity for the first and second wavelengths corresponding to portions of the retina having less oxygenation than the isoreflective points a second false colour and for generating intensities of the first and second false colours at each point in the image proportional to the difference in oxygenation of that respective point from the oxygenation of the isoreflective points.

29. A retinal function camera as claimed in claim 1 further comprising a confocal filter locatable upstream of the imaging and processing means for detecting a retinal surface image and for blocking a deeper choroidal image and an anti-confocal filter locatable upstream of the imaging and processing means to block the retinal surface image and allow the deeper choroidal image to be detected.

30. A retinal function camera as claimed in claim 1 wherein a first linear polarising filter is provided between the light source and the eye and a second linear polarising filter orthogonal to the first linear polarising filter is provided between the eye and the imaging and processing means such that the second orthogonal polarising filter blocks light reflected from a surface of the eye.

31. A retinal function camera as claimed in claim 1, wherein the processing means includes an imaging device sensitive to light emitted by the first source of light and the second source of light.

32. A retinal function camera as claimed in claim 31, wherein the imaging device is one of a CMOS array, a CCD array, a photodetector or an infrared image sensor.

33. A retinal function camera as claimed in claim 1, further comprising optical fibre and lens means for producing a point source of light from light from the first source of light and light from the second source of light.

34. A retinal function camera as claimed in claim 1, further comprising a confocal filter locatable upstream of the imaging and processing means to allow the retinal surface image to be detected while blocking the deeper choroidal image.

35. A retinal function camera as claimed in claim 1 further comprising an anti-confocal filter locatable upstream of the imaging and processing means to block the retinal surface image thereby allowing a deeper choroidal image to be detected.

36. A retinal function camera as claimed in claim 1 wherein synchronising means are provided to synchronise the imaging and processing means with an R wave of a patient's electrocardiogram, to allow retinal metabolism to be studied at different phases of the cardiac cycle.

37. A method of obtaining a retinal function image based on haemoglobin oxygenation the method comprising the steps of:
  a) providing a retinal function camera having a first source of light of a first wavelength band and a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band;
  b) focusing light selectively from the first and second sources on a portion of a retina of an eye;
  c) producing respective images of the portion of the retina illuminated with the respective wavelength bands; and
  d) processing the respective images to determine isoreflective points of the respective images at which absorption of light of the first wavelength is substantially equal to absorption of light of the second wavelength and areas of the respective images having differential absorptivity for the first and second wavelengths to obtain a retinal function image based on haemoglobin oxygenation.

38. A method as claimed in claim 37, wherein the step of processing the images comprises, assigning to first portions of the image corresponding to portions of the retina having greater oxygenation than the isoreflective point a first false colour and generating intensity of the false colours at each point in the image proportional to the flicker contrast that is proportional to the difference in oxygenation of that respective point from the oxygenation of the isoreflective point, assigning to second portions of the image corresponding to portions of the retina having less oxygenation than the isoreflective point a second false colour and generating intensity of the false colours at each point in the image proportional to the flicker contrast that is proportional to the difference in oxygenation of that respective point from the oxygenation of the isoreflective point, assigning a third colour to the isoreflective point, and constructing a composite image by combining the first, second and third colour image data to form a colour image of retinal function based on haemoglobin oxygenation data.

39. A method as claimed in claim 37, wherein the first colour is red.

40. A method as claimed in claim 37, wherein the second colour is blue.

41. A method as claimed in claims 37, wherein the third colour is yellow.

42. A retinal function camera comprising: a first source of light of a first wavelength band; a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band; means for focusing light selectively from the first and second sources on a portion of a retina of an eye; imaging means for producing respective images of a portion of the retina illuminated with the respective wavelength bands; and processing means adapted to process the respective images obtained by the imaging means to determine isoreflective points of the respective images at which absorption of light of the first wavelength is substantially equal to absorption of light of the second wavelength and areas of the respective images having differential absorptivity for the first and second wavelengths, to obtain a retinal function image based on haemoglobin oxygenation, wherein the processing means comprises means for displaying the respective images alternately, at a predetermined frequency, such that the areas of the respective images having differential absorptivity at the first and second wavelengths, flicker.

43. A method of obtaining a retinal function image based on haemoglobin oxygenation the method comprising the steps of:
  a) providing a retinal function camera having a first source of light of a first wavelength band and a second source of light of a second wavelength band, the absorptivity of light of the first wavelength band by oxygenated blood being greater than the absorptivity of light of the second wavelength band and the absorptivity of light of the first wavelength band by deoxygenated blood being less than the absorptivity of light of the second wavelength band;
  b) focusing light selectively from the first and second sources on a portion of a retina of an eye;
  c) producing respective images of the portion of the retina illuminated with the respective wavelength bands; and
  d) processing the respective images to determine isoreflective points of the respective images at which absorption of light of the first wavelength is substantially equal to absorption of light of the second wavelength and areas of the respective images having differential absorptivity for the first and second wavelengths to obtain a retinal function image based on haemoglobin oxygenation;
wherein the step of processing the images comprises, assigning to first portions of the image corresponding to portions of the retina having greater oxygenation than the isoreflective point a first false colour and generating intensity of the false colours at each point in the image proportional to a flicker contrast that is proportional to the difference in oxygenation of that respective point from the oxygenation of the isoreflective point, assigning to second portions of the image corresponding to portions of the retina having less oxygenation than the isoreflective point a second false colour and generating intensity of the false colours at each point in the image proportional to the flicker contrast that is proportional to the difference in oxygenation of that respective point from the oxygenation of the isoreflective point, assigning a third colour to the isoreflective point, and constructing a composite image by combining the first, second and third colour image data to form a colour image of retinal function based on haemoglobin oxygenation data.

* * * * *